United States Patent
Neto et al.

(12) 
(10) Patent No.: US 7,390,911 B2
(45) Date of Patent: Jun. 24, 2008

(54) METHOD FOR PRODUCING PHTHALIC ANHYDRIDE

(75) Inventors: Samuel Neto, Mannheim (DE); Jürgen Zühlke, Speyer (DE); Sebastian Storck, Mannheim (DE); Frank Rosowski, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 394 days.

(21) Appl. No.: 10/557,705

(22) PCT Filed: May 15, 2004

(86) PCT No.: PCT/EP2004/005246

§ 371 (c)(1),
(2), (4) Date: Nov. 22, 2005

(87) PCT Pub. No.: WO2004/103944

PCT Pub. Date: Dec. 2, 2004

(65) Prior Publication Data

US 2007/0066836 A1    Mar. 22, 2007

(30) Foreign Application Priority Data

May 23, 2003  (DE) ............................... 103 23 817

(51) Int. Cl.
*C07D 307/89* (2006.01)
(52) U.S. Cl. ...................................................... 549/249
(58) Field of Classification Search ................ 549/249
See application file for complete search history.

(56) References Cited

FOREIGN PATENT DOCUMENTS

| EP | 0286448 | 10/1988 |
|---|---|---|
| EP | 0539878 | 5/1993 |
| EP | 0906783 | 4/1999 |
| EP | 0985648 | 3/2000 |
| EP | 1 063 222 | 12/2000 |
| WO | WO-03/070680 | 8/2003 |

*Primary Examiner*—Taofiq Solola
(74) *Attorney, Agent, or Firm*—Connolly Bove Lodge & Hutz, LLP

(57) ABSTRACT

The invention relates to a process for preparing phthalic anhydride, in which the catalytic gas-phase oxidation of o-xylene and/or naphthalene is carried out over at least three zones of catalysts of increasing activity, with only the last zone of the catalyst system containing phosphorus and the last zone also comprising at least 10% by weight of vanadium (calculated as $V_2O_5$) based on the active composition of the catalyst and having a ratio of vanadium (calculated as $V_2O_5$) to phosphorus of greater than 35.

20 Claims, No Drawings

METHOD FOR PRODUCING PHTHALIC ANHYDRIDE

This application claims priority from PCT/EP04/005246 filed May 15, 2004 and German Application 103 23 817.4 filed May 23, 2003, the disclosures of each application are incorporated herein by reference.

The present invention relates to a process for preparing phthalic anhydride by catalytic gas-phase oxidation of xylene and/or naphthalene by means of a gas comprising molecular oxygen in a fixed bed using at least three catalysts which are arranged above one another in zones and whose activity increases from zone to zone from the gas inlet end to the gas outlet end and to whose core of support material a layer of catalytically active metal oxides has been applied.

Phthalic anhydride is prepared industrially by catalytic gas-phase oxidation of o-xylene or naphthalene in shell-and-tube reactors. The starting material is a mixture of a gas comprising molecular oxygen, for example air, and the o-xylene and/or naphthalene to be oxidized. The mixture is passed through a multiplicity of tubes arranged in a reactor (shell-and-tube reactor), in each of which a bed of at least one catalyst is located. In recent years, it has become normal practice to arrange catalysts of differing activity in zones in the catalyst bed, with the less active catalyst generally being located toward the gas inlet end in the uppermost, first catalyst zone and the more active catalyst being located toward the gas outlet end in the bottommost, last catalyst zone. This was initially realized in two superposed zones, viz. an upper zone and a lower zone (e.g. DE-A 40 13 051, DE-A 197 07 943, DE-A 25 46 268, U.S. Pat. No. 4,469,878, EP-A 539 878, EP-A 286 448, EP-A 906 783). Over the last few years, it has become usual to use a catalyst system consisting of three superposed zones, viz. an upper zone, a middle zone and a lower zone. This measure enables the activity of the catalyst system in the reactor to be matched to the course of the reaction. In the bottom zone nearest the gas outlet, mostly residual o-xylene or naphthalene and intermediates such as o-tolualdehyde and phthalide are converted into phthalic anhydride. Furthermore, though, by-products such as quinones are also oxidized further.

There are many possible ways of structuring the activity. In the following discussion of the prior art, particular attention will be paid to the last catalyst zone, in particular its phosphorus and vanadium contents and the ratio of these (calculated as $V_2O_5$ to P). Despite many variations of these pairs of values in the prior art, there is still a need for optimization in respect of the activity and selectivity of the last catalyst zone.

DE-A 198 23 262 describes a process for preparing phthalic anhydride using three coated catalysts arranged above one another in zones, with the catalyst activity increasing from zone to zone from the gas inlet end to the gas outlet end and being controlled via the amount of active composition applied and doping with alkali. In the examples, phosphorus is used in the second and third zones. Vanadium pentoxide is used in an amount of less than 10% by weight in the last zone, and the ratio of $V_2O_5$ to P is 37.

EP-A 985 648 describes the preparation of phthalic anhydride by catalytic gas-phase oxidation of o-xylene and/or naphthalene using a catalyst system which is structured so that the "porosity" of the catalyst and thus the activity increases pseudocontinuously from the reactor inlet to the reactor outlet. The porosity is defined as the free volume between the coated shaped bodies of the bed in the reaction tube. In the examples, the structuring of the activity is achieved by arranging at least three different catalysts in series, with the first two zones being free of phosphorus and the lower zone containing from 0.65 to 0.87% by weight of phosphorus and from 15 to 20% by weight of vanadium pentoxide at a $V_2O_5$/P ratio of from 17 to 31. The BET surface area of the catalytically active components is from 70 to 160 $m^2/g$.

WO 03/70680 describes a multizone catalyst system. The structuring of the activity is achieved via the amount of active composition on the support, via the amount of dopants in the form of alkali metal compounds added to the active composition and via the temperature profile. It is stated that the last two zones comprise phosphorus, that from 6 to 9% by weight of vanadium pentoxide are present in the last zone and that the ratio of $V_2O_5$ to P is from 12 to 90.

EP-A 1063222 describes the use of three-zone or multizone catalysts. The activity of the individual zones is altered via the amount of phosphorus in the active composition, the amount of active composition on the support ring, the amount of alkali dopant in the active composition and the fill height of the individual catalyst zones in the reaction tube. The examples describe catalyst systems in which phosphorus is present in all zones and the last zone contains from 0.1 to 0.4% by weight of phosphorus and about 5% by weight of vanadium (calculated as $V_2O_5$) and has a ratio of $V_2O_5$ to P of from 14 to 40.

The increase in activity can accordingly be achieved by means of the following measures or combinations thereof:

(1) by means of a continual increase in the phosphorus content, (2) by means of a continual increase in the active composition content, (3) by means of a continual decrease in the alkali content, (4) by means of a continual decrease in the empty space between the individual catalysts, (5) by means of a continual decrease in the content of inert materials or (6) by means of a continual increase in the temperature from the upper zone (gas inlet) to the lower zone (gas outlet).

The activity of all catalysts decreases as a result of aging processes over their operating life. This occurs particularly in the main reaction zone (upper zone), since the temperatures are highest there. As the period of operation of the catalyst increases, the main reaction zone migrates ever deeper into the catalyst bed. As a result, intermediates and by-products can no longer be reacted completely, since the main reaction zone is then located in catalyst zones which are less selective and more active. The product quality of the phthalic anhydride produced thus deteriorates to an increasing extent. The slowing of the reaction and the associated deterioration in the product quality can be countered by increasing the reaction temperature, for example by increasing the salt bath temperature. However, this increase in temperature results in a decrease in the yield of phthalic anhydride.

Furthermore, the higher the loading of the air with the hydrocarbon to be oxidized, the greater the amounts of intermediates and by-products present in the product, since a high loading increases the migration of the main reaction zone deeper into the catalyst bed. However, high loadings of from 60 to 120 g/standard $m^3$ are desirable for economical production.

The by-products which increase in quantity as aging occurs, particularly when combined with a high loading, comprise not only phthalide (PHD) but also, in particular, anthraquinonedicarboxylic acid (ADCA) and benzoylphthalic anhydride (benzoyl-PA) and unreacted o-xylene. Improvements have been able to be achieved in the amount of PHD present (for example in DE-A-198 23 262). However, there continues to be a need for optimization with regard to general by-product formation, especially in respect of ADCA, since traces of these compounds lead to a yellow coloration of the phthalic anhydride. In addition, a reduction in the amount of these by-products would simplify the work-up of the crude phthalic anhydride.

It is an object of the present invention to provide a process for preparing phthalic anhydride which despite a high loading gives phthalic anhydride having an improved product quality at the same or better yield. Apart from the reduction in the total by-product content, the amount of by-produced ADCA in particular should be reduced at the same or better yield.

We have found that, surprisingly, this object is achieved by a process for preparing phthalic anhydride by catalytic gas-phase oxidation of xylene and/or naphthalene by means of a gas comprising molecular oxygen in a fixed bed using at least three catalysts which are arranged above one another in zones and whose activity increases from zone to zone from the gas inlet end to the gas outlet end and to whose core of support material a layer of catalytically active metal oxides has been applied, wherein only the last catalyst zone comprises phosphorus, at least 10% by weight of vanadium (calculated as $V_2O_5$) based on the active composition of the catalyst is present in the last zone and the ratio of vanadium (calculated as $V_2O_5$) to phosphorus is greater than 35.

The upper catalyst zones are free of phosphorus. The last, bottommost catalyst zone preferably has a phosphorus content of less than 1% by weight (calculated as P) based on the active composition of the catalyst, preferably less than 0.5% by weight, in particular from about 0.05 to 0.4% by weight.

The bed length of the last catalyst zone is preferably less than 40% of the total catalyst bed length of all zones; in particular, the bed length of the last zone is less than 30%, particularly preferably less than 25%, of the total bed length of all zones. The minimum bed length of this zone is generally 16%.

The bed length of the first catalyst zone (upper zone) in a 3-zone catalyst system preferably makes up from 27 to 60%, in particular from 40 to 55%, of the total catalyst fill height in the reactor. The bed length of the middle zone preferably makes up from 15 to 55%, preferably from 20 to 40%, of the total bed length. In the case of a 4-zone catalyst system, the upper zone advantageously makes up from 27 to 55%, in particular from 32 to 47%, of the total bed height in the reactor, the upper middle zone 1 advantageously makes up from 5 to 22%, preferably from 8 to 18%, of the total bed height, and the lower middle zone 2 advantageously makes up from 8 to 35%, in particular from 12 to 30%, of the total bed height. The catalyst zones can also be distributed over a plurality of reactors if desired. Typical reactors have a fill height of from 2.5 to 3.4 meters.

The last, bottommost catalyst zone preferably comprises more than 15% by weight of vanadium (calculated as $V_2O_5$) based on the active composition of the catalyst, in particular from 18 to 22% by weight.

The ratio of vanadium (calculated as $V_2O_5$) to phosphorus (calculated as P) in the last catalyst zone is advantageously about 40 and greater than 40, preferably from 45 to 100, particularly preferably from 50 to 70.

The alkali content of the active composition advantageously decreases from the uppermost catalyst zone to the middle zones. It is advantageous for no alkali to be present in the last catalyst zone. In the first, uppermost catalyst zone, the alkali content is advantageously less than 1.1% by weight of alkali (calculated as alkali metal) based on the active composition of the catalyst; the alkali content is preferably in the range from 0.1 to 0.8% by weight of alkali. In the middle catalyst zone(s), the alkali content is advantageously from 0.05 to 0.6% by weight (calculated as alkali metal) based on the active composition of the catalyst, in particular from 0.05 to 0.3% by weight. Preference is given to using cesium as alkali metal. Alkali metal in the active composition can be partly replaced by alkaline earth metal such as barium, calcium or magnesium.

The BET surface area of the catalytically active components of the catalyst is advantageously in the range from 5 to 50 m² µg, preferably from 5 to 30 m²/g, in particular from ~9 to 27 m²/g.

The proportion of active composition is preferably from 3 to 15% by weight, in particular from 4 to 12% by weight, based on the total mass of the catalyst.

The ADCA content at a loading of at least 80 g of o-xylene/ standard m³ of air is advantageously less than 100 ppm, in particular less than 75 ppm, at a yield of about 113% (phthalic anhydride obtained in percent by weight based on 100% pure o-xylene), which is comparable to or better than that of the prior art. The benzoyl-PA content is advantageously less than 20 ppm, in particular less than 15 ppm.

In a preferred embodiment of a three-zone catalyst system,
a) the least active catalyst comprises, on a nonporous and/ or porous support material, from 7 to 10% by weight, based on the total catalyst, of active composition comprising from 6 to 11% by weight of $V_2O_5$, from 0 to 3% by weight of $Sb_2O_3$, 0% by weight of P, from 0.1 to 1.1% by weight of alkali (calculated as alkali metal) and $TiO_2$ in anatase form as balance,
b) the next most active catalyst comprises, on a nonporous and/or porous support material, from 7 to 12% by weight, based on the total catalyst, of active composition comprising from 5 to 13% by weight of $V_2O_5$, from 0 to 3% by weight of $Sb_2O_3$, 0% by weight of P, from 0 to 0.4% by weight of alkali (calculated as alkali metal) and $TiO_2$ in anatase form as balance,
c) and the most active catalyst comprises, on a nonporous and/or porous support material, from 8 to 12% by weight, based on the total catalyst, of active composition comprising from 10 to 30% by weight of $V_2O_5$, from 0 to 3% by weight of $Sb_2O_3$, from 0 to 0.43% by weight of P, from 0 to 0.1% by weight of alkali (calculated as alkali metal) and $TiO_2$ in anatase form as balance, with preference being given to using cesium as alkali metal.

The titanium dioxide in anatase form which is used advantageously has a BET surface area of from 5 to 50 m²/g, in particular from 15 to 30 m² µg. It is also possible to use mixtures of titanium dioxide in anatase form having different BET surface areas, provided that the resulting BET surface area is in the range from 15 to 30 m²/g. The individual catalyst zones can also contain titanium dioxide having different BET surface areas. The BET surface area of the titanium dioxide used preferably increases from the upper zone a) to the lower zone c).

In a preferred embodiment of a four-zone catalyst system,
a) the least active catalyst comprises, on a nonporous and/ or porous support material, from 7 to 10% by weight, based on the total catalyst, of active composition comprising from 6 to 11% by weight of $V_2O_5$, from 0 to 3% by weight of $Sb_2O_3$, 0% by weight of P, from 0.1 to 1.1% by weight of alkali (calculated as alkali metal) and $TiO_2$ in anatase form as balance,
b1) the next most active catalyst comprises, on a nonporous and/or porous support material, from 7 to 12% by weight, based on the total catalyst, of active composition comprising from 4 to 15% by weight of $V_2O_5$, from 0 to 3% by weight of $Sb_2O_3$, 0% by weight of P, from 0.1 to 1% by weight of alkali (calculated as alkali metal) and TiO$_2$ in anatase form as balance, b2) the next most active catalyst comprises, on a nonporous and/or porous support material, from 7 to 12% by weight, based on the total catalyst, of active composition comprising from 5 to 15% by weight of V$_2$O$_5$, from 0 to 3% by weight of Sb$_2$O$_3$, 0% by weight of P, from 0 to 0.4% by weight of alkali (calculated as alkali metal) and TiO$_2$ in anatase form as balance, c) and the most active catalyst comprises, on a nonporous and/or porous support material, from 8 to 12% by weight, based on the total catalyst, of active composition comprising from 10 to 30% by weight of V$_2$O$_5$, from 0 to 3% by weight of Sb$_2$O$_3$, from 0 to 0.43% by weight of P, from 0 to 0.1% by weight of alkali (calculated as alkali metal) and TiO$_2$ in anatase form as balance, with preference being given to using cesium as alkali metal.

Preference is given to using from three to five zones.

In general, the catalyst zones, e.g. a), b1), b2) and/or c), can also be arranged so that each of them consists of two or more zones. These intermediate zones preferably have intermediate catalyst compositions.

In place of delineated zones of the various catalysts, a pseudocontinuous transition from zone to zone and an effectively uniform increase in the activity can also be obtained by the transition from one zone to the next zone being made up of a zone consisting of a mixture of the successive catalysts.

Oxidic supported catalysts are suitable as catalysts. To prepare phthalic anhydride by gas-phase oxidation of o-xylene or naphthalene or mixtures thereof, use is generally made of spherical, annular or dish-shaped supports comprising a silicate, silicon carbide, porcelain, aluminum oxide, magnesium oxide, tin dioxide, rutile, aluminum silicate, magnesium silicate (steatite), zirconium silicate or cerium silicate or mixtures thereof. Coated catalysts in which the catalytically active composition has been applied in the form of a shell to the support are particularly suitable. The active composition preferably comprises vanadium pentoxide as catalytically active constituent in addition to titanium dioxide. Furthermore, the catalytically active composition can comprise small amounts of many other oxidic compounds which act as promoters to influence the activity and selectivity of the catalyst, for example by reducing or increasing its activity. Such promoters are, for example, the alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony Oxide, cerium oxide and phosphorus pentoxide. The alkali metal oxides act, for example, as promoters which reduce the activity and increase the selectivity. Furthermore, organic binders, preferably copolymers, advantageously in the form of an aqueous dispersion, of vinyl acetate-vinyl laurate, vinyl acetate-acrylate, styrene-acrylate, vinyl acetate-maleate, vinyl acetate-ethylene, and also hydroxyethylcellulose can be added to the catalytically active composition in amounts of from 3 to 20% by weight, based on the solids content of the solution of the constituents of the active composition (EP-A 744 214). Preference is given to using organic binders as described in DE-A 198 24 532. If the catalytically active composition is applied to the support without organic binders, coating temperatures above 150° C. are advantageous. When the abovementioned binders are added, the usable coating temperatures are, depending on the binder used, in the range from 50 to 450° C. (DE-A 21 06 796). The binders applied burn out within a short time after installation of the catalyst and start-up of the reactor. The additional binder has the additional advantage that the active composition adheres well to the support, so that transport and installation of the catalyst are made easier.

To carry out the reaction, the catalysts are introduced in zones into the tubes of a shell-and-tube reactor. The least active catalyst is positioned in the fixed bed so that the reaction gas firstly comes into contact with this catalyst and only subsequently comes into contact with the next most active catalyst in the following zone. The reaction gas subsequently comes into contact with the still more active catalyst zones. The catalysts of differing activity can be thermostated to the same temperature or to different temperatures.

The reaction gas is generally passed over the resulting catalyst bed at from 300 to 450° C., preferably from 320 to 420° C. and particularly preferably from 340 to 400° C. A 15' gauge pressure of generally from 0.1 to 2.5 bar, preferably from 0.3 to 1.5 bar, is advantageously used. The space velocity is generally from 750 to 5000 h$^{-1}$.

The reaction gas supplied to the catalyst (starting gas mixture) is generally produced by mixing a gas which comprises molecular oxygen and may further comprise suitable reaction moderators such as nitrogen and/or diluents such as steam and/or carbon dioxide in addition to oxygen with the aromatic hydrocarbon to be oxidized. The gas comprising molecular oxygen may generally comprise from 1 to 100 mol %, preferably from 2 to 50 mol % and particularly preferably from 10 to 30 mol %, of oxygen, from 0 to 30 mol %, preferably from 0 to 10 mol %, of water vapor and from 0 to 50 mol %, preferably from 0 to 1 mol %, of carbon dioxide, balance nitrogen. To produce the reaction gas, the gas comprising molecular oxygen is generally loaded with from 30 g to 150 g of the aromatic hydrocarbon to be oxidized per standard m$^3$ of gas, in particular with from 60 to 120 g of the aromatic hydrocarbon to be oxidized per standard m$^3$ of gas.

In general, the reaction is carried out so that the major part of the o-xylene and/or naphthalene present in the reaction gas is reacted in the first reaction zone.

The hot spot temperature of the uppermost zone is preferably from 400 to 470° C., and in the middle zone or zones of a multizone catalyst system it is advantageously less than 420° C., in particular less than 410° C.

If desired, a downstream finishing reactor as is described, for example, in DE-A 198 07 018 or DE-A 20 05 969 can be provided for the preparation of phthalic anhydride. The catalyst used in this finishing reactor is preferably a catalyst having an even higher activity than that of the bottommost zone.

According to the present invention, phthalic anhydride can be prepared in a high yield with a low concentration of by-products, in particular a very small amount of ADCA and benzoyl PA, even at high loadings with o-xylene and/or naphthalene.

EXAMPLES

A. Production of the Catalysts

A.1 Production of Catalyst 1 (3-Zone Catalyst)

Upper Zone (a)

35.32 g of anatase (TiO$_2$-1, BET surface area=9 m$^2$ µg), 65.58 g of anatase (TiO$_2$-2, BET surface area=20 m$^2$ µg), 7.97 g of vanadium pentoxide, 2.65 g of antimony oxide, 0.45 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, external diameter (ED)×length (L)×internal diameter (ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.33% by weight of cesium (calculated as Cs), 31.54% by weight of titanium dioxide ($TiO_2$-1) and 58.56% by weight of titanium dioxide ($TiO_2$-2) after calcination at 450° C. for one hour.

Middle Zone (b)

24.16 g of anatase ($TiO_2$-1, BET surface area=9 m$^2$/g), 72.48 g of anatase ($TiO_2$-2, BET surface area=20 m$^2$/g), 7.74 g of vanadium pentoxide, 2.57 g of antimony trioxide, 0.13 g of cesium carbonate were suspended in 650 ml of deionized water and stirred for 18 hours to achieve homogeneous dispersion. 60 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.10% by weight of cesium (calculated as Cs), 22.23% by weight of titanium dioxide ($TiO_2$-1) and 66.68% by weight of titanium dioxide ($TiO_2$-2) after calcination at 450° C. for one hour.

Lower Zone (c)

22.07 g of anatase ($TiO_2$-1, BET surface area=9 m$^2$/g), 88.28 g of anatase ($TiO_2$-2, BET surface area=27 m$^2$/g), 28.07 g of vanadium pentoxide, 1.93 g of ammonium dihydrogenphosphate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 20.0% by weight of vanadium (calculated as $V_2O_5$), 0.37% by weight of phosphorus (calculated as P), 15.73% by weight of titanium dioxide ($TiO_2$-1) and 62.90% by weight of titanium dioxide ($TiO_2$-3) after calcination at 450° C. for one hour.

A.2. Production of Catalyst 2 (4-Zone Catalyst)

Upper Zone (a)

29.27 g of anatase ($TiO_2$-1, BET surface area=9 m$^2$/g), 69.80 g of anatase ($TiO_2$-2, BET surface area=21 m$^2$/g), 7.83 g of vanadium pentoxide, 2.61 g of antimony oxide, 0.49 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.36% by weight of cesium (calculated as Cs), 27.20% by weight of titanium dioxide ($TiO_2$-1) and 63.46% by weight of titanium dioxide ($TiO_2$-2) after calcination at 450° C. for one hour.

Middle Zone 1 (b1)

24.61 g of anatase ($TiO_2$-1, BET surface area=9 m$^2$/g), 74.46 g of anatase ($TiO_2$-2, BET surface area=21 m$^2$/g), 7.82 g of vanadium pentoxide, 2.60 g of antimony oxide, 0.35 g of cesium carbonate were suspended in 650 ml of deionized water and stirred for 18 hours to achieve homogeneous dispersion. 50 g of organic-binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.26% by weight of cesium (calculated as Cs), 22.60% by weight of titanium dioxide ($TiO_2$-1) and 67.79% by weight of titanium dioxide ($TiO_2$-2) after calcination at 450° C. for one hour.

Middle Zone 2 (b2)

24.82 g of anatase ($TiO_2$-1, BET surface-area=9 m$^2$/g), 74.46 g of anatase ($TiO_2$-2, BET surface area=21 m$^2$/g), 7.82 g of vanadium pentoxide, 2.60 g of antimony oxide, 0.135 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as $V_2O_5$), 2.37% by weight of antimony (calculated as $Sb_2O_3$), 0.10% by weight of cesium (calculated as Cs), 22.60% by weight of titanium dioxide ($TiO_2$-1) and 67.79% by weight of titanium dioxide ($TiO_2$-2) after calcination at 450° C. for one hour.

Lower Zone (c)

17.23 g of anatase ($TiO_2$-1, BET surface area=9 m$^2$/g), 69.09 g of anatase ($TiO_2$-2, BET surface area=27 m$^2$/g), 21.97 g of vanadium pentoxide, 1.55 g of ammonium dihydrogenphosphate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 20.0% by weight of vanadium (calculated as $V_2O_5$), 0.38% by weight of phosphorus (calculated as P), 15.73% by weight of titanium dioxide (TiO$_2$-1) and 62.90% by weight of titanium dioxide (TiO$_2$-2) after calcination at 450° C. for one hour.

A.3. Production of Catalyst 3 (P-Doped Middle Zone—3-zone catalyst—comparative example 1)

Upper Zone (a)

35.32 g of anatase (TiO$_2$-1, BET surface area=9 m$^2$ μg), 65.58 g of anatase (TiO$_2$-2, BET surface area=20 m$^2$/g), 7.97 g of vanadium pentoxide, 2.65 g of antimony oxide, 0.45 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.33% by weight of cesium (calculated as Cs), 31.54% by weight of titanium dioxide (TiO$_2$-1) and 58.56% by weight of titanium dioxide (TiO$_2$-2) after calcination at 450° C. for one hour.

Middle Zone (b)

34.32 g of anatase (TiO$_2$-1, BET surface area=9 m$^2$ μg), 102.90 g of anatase (TiO$_2$-2, BET surface area=20 m$^2$/g), 10.99 g of vanadium pentoxide, 3.66 g of antimony trioxide, 2.30 g of ammonium dihydrogenphosphate and 0.19 g of cesium carbonate were suspended in 650 ml of deionized water and stirred for 18 hours to achieve homogeneous dispersion. 52 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.40% by weight of phosphorus (calculated as P), 0.10% by weight of cesium (calculated as Cs), 22.23% by weight of titanium dioxide (TiO$_2$-1) and 66.68% by weight of titanium dioxide (TiO$_2$-2) after calcination at 450° C. for one hour.

Lower Zone (c)

22.07 g of anatase (TiO$_2$-1, BET surface area ~9 m$^2$ μg), 88.28 g of anatase (TiO$_2$-3, BET surface area=27 m$^2$/g), 28.07 g of vanadium pentoxide, 1.93 g of ammonium dihydrogenphoshate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 20.0% by weight of vanadium (calculated as V$_2$O$_5$), 0.37% by weight of phosphorus (calculated as P), 15.73% by weight of titanium dioxide (TiO$_2$-1) and 62.90% by weight of titanium dioxide (TiO$_2$-3) after calcination at 450° C. for one hour.

A.4. Production of catalyst 4 (P-Doped Upper Zone and Middle Zone —3-Zone Catalyst—Comparative Example 2)

Upper Zone (a)

35.32 g of anatase (TiO$_2$-1, BET surface area=9 m$^2$/g), 67.96 g of anatase (TiO$_2$-2, BET surface area=20 m$^2$/g), 8.26 g of vanadium pentoxide, 2.75 g of antimony oxide, 1.29 g of ammonium dihydrogenphosphate, 0.47 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.30% by weight of phosphorus (calculated as P), 0.33% by weight of cesium (calculated as Cs), 31.54% by weight of titanium dioxide (TiO$_2$-1) and 58.56% by weight of titanium dioxide (TiO$_2$-2) after calcination at 450° C. for one hour.

Middle Zone (b)

34.32 g of anatase (TiO$_2$-1, BET surface area=9 m$^2$/g), 102.90 g of anatase (TiO$_2$-2, BET surface area=20 m$^2$/g), 10.99 g of vanadium pentoxide, 3.66 g of antimony trioxide, 2.30 g of ammonium dihydrogenphosphate and 0.19 g of cesium carbonate were suspended in 650 ml of deionized water and stirred for 18 hours to achieve homogeneous dispersion. 52 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.40% by weight of phosphorus (calculated as P), 0.10% by weight of cesium (calculated as Cs), 22.23% by weight of titanium dioxide (TiO$_2$-1) and 66.68% by weight of titanium dioxide (TiO$_2$-2) after calcination at 450° C. for one hour.

Lower Zone (c)

22.07 g of anatase (TiO$_2$-1, BET surface area=9 m$^2$/g), 88.28 g of anatase (TiO$_2$-3, BET surface area=27 m$^2$/g), 28.07 g of vanadium pentoxide, 1.93 g of ammonium dihydrogenphoshate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 20.0% by weight of vanadium (calculated as V$_2$O$_5$), 0.37% by weight of phosphorus (calculated as P), 15.73% by weight of titanium dioxide (TiO$_2$-1) and 62.90% by weight of titanium dioxide (TiO$_2$-3) after calcination at 450° C. for one hour.

A.5. Production of Catalyst 5 (7.12% by Weight of V$_2$O$_5$ in Zone (c), V$_2$O$_5$/P=19.2—3-Zone Catalyst—Comparative Example 3)

Upper Zone (a)

35.32 g of anatase (TiO$_2$-1, BET surface area=9 m$^2$/g), 65.58 g of anatase (TiO$_2$-2, BET surface area=20 m$^2$/g), 7.97 g of vanadium pentoxide, 2.65 g of antimony oxide, 0.45 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.33% by weight of cesium (calculated as Cs), 31.54% by weight of titanium dioxide (TiO$_2$-1) and 58.56% by weight of titanium dioxide (TiO$_2$-2) after calcination at 450° C. for one hour.

Middle Zone (b)

24.16 g of anatase (TiO$_2$-1, BET surface area=9 m$^2$/g), 72.48 g of anatase (TiO$_2$-2, BET surface area=20 m$^2$ μg), 7.74 g of vanadium pentoxide, 2.57 g of antimony trioxide, 0.13 g of cesium carbonate were suspended in 650 ml of deionized water and stirred for 18 hours to achieve homogeneous dispersion. 60 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium-silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.10% by weight of cesium (calculated as Cs), 22.23% by weight of titanium dioxide (TiO$_2$-1) and 66.68% by weight of titanium dioxide (TiO$_2$-2) after calcination at 450° C. for one hour.

Lower Zone (c)

40.15 g of anatase (TiO$_2$-1, BET surface area=9 m$^2$/g), 88.28 g of anatase (TiO$_2$-3, BET surface area=27 m$^2$/g), 9.99 g of vanadium pentoxide, 1.93 g of ammonium dihydrogenphoshate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as V$_2$O$_5$), 0.37% by weight of phosphorus (calculated as P), 15.73% by weight of titanium dioxide (TiO$_2$-1) and 62.90% by weight of titanium dioxide (TiO$_2$-3) after calcination at 450° C. for one hour.

A.6 Production of Catalyst 6 (11.5% by Weight of V$_2$O$_5$ in Zone (c), V$_2$O$_5$/P=31.1—3-Zone Catalyst—Comparative Example 4)

Upper Zone (a)

35.32 g of anatase (TiO$_2$-1, BET surface area=9 m$^2$ μg), 65.58 g of anatase (TiO$_2$-2, BET surface area=20 m$^2$/g), 7.97 g of vanadium pentoxide, 2.65 g of antimony oxide, 0.45 g of cesium carbonate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 8% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.33% by weight of cesium (calculated as Cs), 31.54% by weight of titanium dioxide (TiO$_2$-1) and 58.56% by weight of titanium dioxide (TiO$_2$-2) after calcination at 450° C. for one hour.

Middle Zone (b)

24.16 g of anatase (TiO$_2$-1, BET surface area=9 m$^2$/g), 72.48 g of anatase (TiO$_2$-2, BET surface area=20 m$^2$/g), 7.74 g of vanadium pentoxide, 2.57 g of antimony trioxide, 0.13 g of cesium carbonate were suspended in 650 ml of deionized water and stirred for 18 hours to achieve homogeneous dispersion. 60 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 7.12% by weight of vanadium (calculated as V$_2$O$_5$), 2.37% by weight of antimony (calculated as Sb$_2$O$_3$), 0.10% by weight of cesium (calculated as Cs), 22.23% by weight of titanium dioxide (TiO$_2$-1) and 66.68% by weight of titanium dioxide (TiO$_2$-2) after calcination at 450° C. for one hour.

Lower Zone (c)

34.00 g of anatase (TiO$_2$-1, BET surface area=9 m$^2$/g), 88.28 g of anatase (TiO$_2$-3, BET surface area=27 m$^2$/g), 16.14 g of vanadium pentoxide, 1.93 g of ammonium dihydrogenphoshate were suspended in 650 ml of deionized water and stirred for 18 hours to achieve homogeneous dispersion. 50 g of organic binder consisting of a copolymer of vinyl acetate and vinyl laurate in the form of a 50% strength by weight aqueous dispersion were added to this suspension. The suspension obtained was subsequently sprayed onto 1200 g of steatite (magnesium silicate) in the form of rings (7×7×4 mm, (ED)×(L)×(ID)) and dried. The weight of the shell applied was 10% of the total weight of the finished catalyst. The catalytically active composition applied in this way, i.e. the catalyst shell, comprised 11.50% by weight of vanadium (calculated as V$_2$O$_5$), 0.37% by weight of phosphorus (calculated as P), 15.73% by weight of titanium dioxide (TiO$_2$-1) and 62.90% by weight of titanium dioxide (TiO$_2$-3) after calcination at 450° C. for one hour.

B Oxidation of G-Xylene to PA

B.1 3-Zone Catalyst

From the bottom upward, 0.70 m of the catalyst of the lower zone (c), 0.60 m of the catalyst of the middle zone (b) and 1.50 m of the catalyst of the upper zone (a) were each introduced into a 3.85 m long iron tube having an internal diameter of 25 mm. The iron tube was surrounded by: a salt melt to regulate the temperature, and a 2 mm thermo well containing a thermocouple which could be moved up and down was employed for measuring the catalyst temperature. 4 standard $m^3$ of air having loadings of 98.5% by weight pure o-xylene of from 0 to 100 g/standard $m^3$ were passed through the tube per hour from the top downward. After a running time of 10-14 days, the introduction of o-xylene was interrupted and the catalyst was exposed to the following conditions for a period of 72 hours: salt bath temperature (SBT) of 410° C., air flow=2 standard $m^3$/h. At an o-xylene loading of 60-100 g/standard $m^3$, the results summarized in Tables 1 and 2 were obtained ("PA yield" is the amount of PA obtained in percent by weight, based on 100% pure o-xylene).

B.2 4-Zone Catalyst

From the bottom upward, 0.70 m of the catalyst of the lower zone (c), 0.70 m of the catalyst of the middle zone 2 (b2), 0.50 m of the catalyst of the middle zone 1 (b1) and 1.30 m of the catalyst of the upper zone (a) were each introduced into a 3.85 m long iron tube having an internal diameter of 25 mm. Otherwise, the experiment was carried out as indicated in B.1.

The experimental results after activation are summarized in Tables 1 and 2.

The following abbreviations were used:

| | |
|---|---|
| HST | hot spot temperature |
| UZ | upper zone |
| MZ | middle zone |
| LZ | lower zone |
| ROG | reaction outlet gas |
| SBT | salt bath temperature |
| PHD | phthalide |
| PA | phthalic anhydride |
| Benzoyl-PA | 4-benzoylphthalic anhydride |
| ADCA | anthraquinonedicarboxylic anhydride |

TABLE 1

Preparation of PA at an o-xylene loading of 60-80 g/standard $m^3$ using a 3-zone catalyst

| | Catalyst | | | |
|---|---|---|---|---|
| | 1 | 3 | 4 | 5 |
| 3-zone catalysts | according to the present invetion | comparative example 1 | comparative example 2 | comparative example 3 |
| Upper zone | P-free | P-free | 0.30% by weight of P | P-free |
| Middle zone | P-free | 0.40% by weight of P | 0.40% by weight of P | P-free |
| Lower zone: last zone | 20% by weight of $V_2O_5$ 0.37% by weight of P $V_2O_5/P = 54.1$ | 20% by weight of $V_2O_5$ 0.37% by weight of P $V_2O_5/P = 54.1$ | 20% by weight of $V_2O_5$ 0.37% by weight of P $V_2O_5/P = 54.1$ | 7.12% weight of $V_2O_5$ 0.37% by weight of P $V_2O_5/P = 19.2$ |
| Loading [g/standard $m^3$] | 80 | 60 | 58 | 70 |
| SBT [° C.] | 360 | 375 | 375 | 362 |
| Time of operation [d] | 60 | 29 | 16 | 30 |
| HST UZ [° C.] | 426 | 433 | 447 | 447 |
| HST MZ [° C.] | 397 | 416 | 419 | 395 |
| Average PA yield [m/m-%] | 113.0 | 111.5 | 110.5 | 112.0 |
| ADCA [ppm] | 67 | 180 | 325 | 107 |
| Benzoyl-PA [ppm] | 13 | 26 | 27 | 14 |
| Residual o-xylene [% by weight] | 0.004 | 0.012 | 0.010 | 0.011 |
| PHD [% by weight] | 0.030 | 0.050 | 0.060 | 0.068 |

TABLE 2

Preparation of PA at an o-xylene loading of 70-100 g/standard $m^3$ using a 3-zone catalyst and a 4-zone catalyst

| | Catalyst | | |
|---|---|---|---|
| | 1 | 2 | 6 |
| 3- and 4-zone catalysts | according to the present invention | according to the present invention 4-zone cat | comparative example 4 |
| Upper zone | P-free | P-free | P-free |
| Middle zone 1 | P-free | P-free | P-free |
| Middle zone 2 | | P-free | |
| Lower zone: last zone | 20% by weight of $V_2O_5$ 0.37% by weight of P $V_2O_5/P = 54.1$ | 20% by weight of $V_2O_5$ 0.37% by weight of P $V_2O_5/P = 54.1$ | 11.5% by weight of $V_2O_5$ 0.37% by weight of P $V_2O_5/P = 31.1$ |
| Loading [g/standard $m^3$] | 100 | 100 | 70 |
| SBT [° C.] | 358 | 360 | 372 |
| Time of operation [d] | 39 | 52 | 27 |

TABLE 2-continued

Preparation of PA at an o-xylene loading of 70-100 g/standard m³ using a 3-zone catalyst and a 4-zone catalyst

| | Catalyst | | |
|---|---|---|---|
| | 1 | 2 | 6 |
| HST UZ [° C.] | 446 | 440 | 445 |
| HST MZ [° C.] | 429 | 432 | 423 |
| Average PA yield [m/m-%] | 112.5 | 113.5 | 112.2 |
| ADCA [ppm] | 69 | 45 | 82 |
| Benzoyl-PA [ppm] | 15 | 12 | 13 |
| Residual o-xylene [% by weight] | 0.015 | 0.003 | 0.004 |
| PHD [% by weight] | 0.060 | 0.020 | 0.072 |

Composition of the Catalysts (%=% by Weight)

Catalyst 1

| | Catalyst | | |
|---|---|---|---|
| | Upper zone | Middle zone | Lower zone |
| Active composition [%] | 8 | 10 | 10 |
| TiO$_2$-1, 9 m$^2$/g [%] | 31.54 | 22.23 | 15.73 |
| TiO$_2$-2, 20 m$^2$/g [%] | 58.56 | 66.68 | — |
| TiO$_2$-3, 27 m$^2$/g [%] | — | — | 62.90 |
| V$_2$O$_5$ [%] | 7.12 | 7.12 | 20.0 |
| Sb$_2$O$_3$ [%] | 2.37 | 2.37 | — |
| Cs [%] | 0.33 | 0.10 | — |
| P [%] | — | — | 0.37 |

Catalyst 2

| | Catalyst | | | |
|---|---|---|---|---|
| | Upper zone | Middle zone 1 | Middle zone 2 | Lower zone |
| Active composition [%] | 8 | 8 | 8 | 8 |
| TiO$_2$-1, 9 m$^2$/g [%] | 27.20 | 22.60 | 22.60 | 15.73 |
| TiO$_2$-2, 20 m$^2$/g [%] | 63.46 | 67.79 | 67.79 | — |
| TiO$_2$-3, 27 m$^2$/g [%] | — | — | — | 62.90 |
| V$_2$O$_5$ [%] | 7.12 | 7.12 | 7.12 | 20.0 |
| Sb$_2$O$_3$ [%] | 2.37 | 2.37 | 2.37 | — |
| Cs [%] | 0.33 | 0.25 | 0.10 | — |
| P [%] | — | — | — | 0.37 |

Catalyst 3 - Comparative example

| | Catalyst | | |
|---|---|---|---|
| | Upper zone | Middle zone | Lower zone |
| Active composition [%] | 8 | 10 | 10 |
| TiO$_2$-1, 9 m$^2$/g [%] | 31.54 | 22.23 | 15.73 |
| TiO$_2$-2, 20 m$^2$/g [%] | 58.56 | 66.68 | — |
| TiO$_2$-3, 27 m$^2$/g [%] | — | — | 62.90 |
| V$_2$O$_5$ [%] | 7.12 | 7.12 | 20.0 |
| Sb$_2$O$_3$ [%] | 2.37 | 2.37 | — |
| Cs [%] | 0.33 | 0.10 | — |
| P [%] | — | 0.40 | 0.37 |

Catalyst 4 - Comparative example

| | Catalyst | | |
|---|---|---|---|
| | Upper zone | Middle zone | Lower zone |
| Active composition [%] | 8 | 10 | 10 |
| TiO$_2$-1, 9 m$^2$/g [%] | 31.54 | 22.23 | 15.73 |
| TiO$_2$-2, 20 m$^2$/g [%] | 58.56 | 66.68 | — |
| TiO$_2$-3, 27 m$^2$/g [%] | — | — | 62.9 |
| V$_2$O$_5$ [%] | 7.12 | 7.12 | 20.0 |
| Sb$_2$O$_3$ [%] | 2.37 | 2.37 | — |
| Cs [%] | 0.33 | 0.10 | — |
| P [%] | 0.30 | 0.40 | 0.37 |

Catalyst 5 - Comparative example

| | Catalyst | | |
|---|---|---|---|
| | Upper zone | Middle zone | Lower zone |
| Active composition [%] | 8 | 10 | 10 |
| TiO$_2$-1, 9 m$^2$/g [%] | 31.54 | 22.23 | 15.73 |
| TiO$_2$-2, 20 m$^2$/g [%] | 58.56 | 66.68 | — |
| TiO$_2$-3, 27 m$^2$/g [%] | — | — | 62.90 |

-continued

Catalyst 5 - Comparative example

| Catalyst | | | |
|---|---|---|---|
| | Upper zone | Middle zone | Lower zone |
| $V_2O_5$ [%] | 7.12 | 7.12 | 7.12 |
| $Sb_2O_3$ [%] | 2.37 | 2.37 | — |
| Cs [%] | 0.33 | 0.10 | — |
| P [%] | — | — | 0.37 |

Catalyst 6 - Comparative example

| Catalyst | | | |
|---|---|---|---|
| | Upper zone | Middle zone | Lower zone |
| Active composition [%] | 8 | 10 | 10 |
| $TiO_2$-1, 9 m$^2$/g [%] | 31.54 | 22.23 | 15.73 |
| $TiO_2$-2, 20 m$^2$/g [%] | 58.56 | 66.68 | — |
| $TiO_2$-3, 27 m$^2$/g [%] | — | — | 62.90 |
| $V_2O_5$ [%] | 7.12 | 7.12 | 11.50 |
| $Sb_2O_3$ [%] | 2.37 | 2.37 | — |
| Cs [%] | 0.33 | 0.10 | — |
| P [%] | — | — | 0.37 |

We claim:

1. A process for preparing phthalic anhydride by catalytic gas-phase oxidation of xylene and/or naphthalene by means of a gas comprising molecular oxygen in a fixed bed using at least three catalysts which are arranged above one another in zones and whose activity increases from zone to zone from the gas inlet end to the gas outlet end and to whose core of support material a layer of catalytically active metal oxides has been applied, wherein only the last catalyst zone comprises phosphorus, at least 10% by weight of vanadium (calculated as $V_2O_5$) based on the active composition of the catalyst is present in the last zone and the ratio of vanadium (calculated as $V_2O_5$) to phosphorus is greater than 35.

2. A process as claimed in claim 1, wherein the bed length of the last catalyst zone is not more than 40% of the total bed length of all zones.

3. A process as claimed in claim 1, wherein the bed length of the last catalyst zone is not more than 25% of the total bed length of all zones.

4. A process as claimed in claim 1, wherein the ratio of vanadium (calculated as $V_2O_5$) to phosphorus in the last catalyst zone is from 40 to 100.

5. A process as claimed in claim 1, wherein the last catalyst zone comprises at least 15% by weight of vanadium (calculated as $V_2O_5$) based on the active composition of the catalyst.

6. A process as claimed in claim 1, wherein the last catalyst zone comprises from 18 to 22% by weight of vanadium (calculated as $V_2O_5$) based on the active composition of the catalyst.

7. A process as claimed in claim 1, wherein the first catalyst zone comprises less than 1.1% by weight of alkali (calculated as alkali metal) based on the active composition of the catalyst.

8. A process as claimed in claim 1, wherein the first catalyst zone has an alkali content of from 0.1 to 0.8% by weight of alkali (calculated as alkali metal) based on the active composition and the middle catalyst zone(s) has/have an alkali content of from 0.05 to 0.6% by weight (calculated as alkali metal).

9. A process as claimed in claim 1, wherein cesium is used as alkali metal additive.

10. A process as claimed in claim 1, wherein the last catalyst zone comprises less than 1% by weight of phosphorus.

11. A process as claimed in claim 1, wherein the BET surface area of the active composition is from 5 to 50 m$^2$/g.

12. A process as claimed in claim 1, wherein the proportion of active composition based on the total mass of the catalyst is from 3 to 15% by weight.

13. A process as claimed in claim 1, wherein the anthraquinonedicarboxylic acid content of the phthalic anhydride product is less than 75 ppm.

14. A process as claimed in claim 2, wherein the ratio of vanadium (calculated as $V_2O_5$) to phosphorus in the last catalyst zone is from 40 to 100.

15. A process as claimed in claim 3, wherein the ratio of vanadium (calculated as $V_2O_5$) to phosphorus in the last catalyst zone is from 40 to 100.

16. A process as claimed in claim 2, wherein the last catalyst zone comprises at least 15% by weight of vanadium (calculated as $V_2O_5$) based on the active composition of the catalyst.

17. A process as claimed in claim 3, wherein the last catalyst zone comprises at least 15% by weight of vanadium (calculated as $V_2O_5$) based on the active composition of the catalyst.

18. A process as claimed in claim 4, wherein the last catalyst zone comprises at least 15% by weight of vanadium (calculated as $V_2O_5$) based on the active composition of the catalyst.

19. A process as claimed in claim 2, wherein the last catalyst zone comprises from 18 to 22% by weight of vanadium (calculated as $V_2O_5$) based on the active composition of the catalyst.

20. A process as claimed in claim 3, wherein the last catalyst zone comprises from 18 to 22% by weight of vanadium (calculated as $V_2O_5$) based on the active composition of the catalyst.

* * * * *